United States Patent [19]

Lewis et al.

[11] Patent Number: 6,020,579

[45] Date of Patent: *Feb. 1, 2000

[54] MICROWAVE APPLICATOR HAVING A MECHANICAL MEANS FOR TUNING

[75] Inventors: David Andrew Lewis, Carmel; Stanley Joseph Whitehair, Peekskill, both of N.Y.

[73] Assignee: International Business Machines Corporation, Armonk, N.Y.

[ * ] Notice: This patent is subject to a terminal disclaimer.

[21] Appl. No.: 09/002,720

[22] Filed: Jan. 5, 1998

Related U.S. Application Data

[60] Provisional application No. 60/034,718, Jan. 6, 1997.
[51] Int. Cl.⁷ ..................................................... H05B 6/70
[52] U.S. Cl. .......................... 219/696; 219/690; 219/745; 219/750
[58] Field of Search ..................................... 219/678, 679, 219/680, 690, 691, 693, 695, 696, 697, 698, 699, 670, 745, 746, 750, 752

[56] References Cited

U.S. PATENT DOCUMENTS

| | | | |
|---|---|---|---|
| 3,461,261 | 8/1969 | Lewis et al. .............................. | 219/693 |
| 4,507,588 | 3/1985 | Asmussen et al. ....................... | 315/319 |
| 4,585,668 | 4/1986 | Asmussen et al. ....................... | 438/478 |
| 4,630,566 | 12/1986 | Asmussen et al. . | |
| 4,727,293 | 2/1988 | Asmussen et al. ....................... | 315/111.41 |
| 4,777,336 | 10/1988 | Asmussen et al. ....................... | 219/696 |
| 4,792,772 | 12/1988 | Asmussen et al. ....................... | 333/230 |
| 5,471,037 | 11/1995 | Goethal et al. .......................... | 219/750 |

*Primary Examiner*—Tu Ba Hoang
*Attorney, Agent, or Firm*—Ohlandt, Greeley, Ruggiero & Perle

[57] ABSTRACT

A microwave applicator includes an elongated chamber, preferably having a cylindrical shape, for processing materials therein. A waveguide, connected to the elongated chamber, couples microwave power into the elongated chamber. The cross-sectional area of the elongated chamber can be mechanically adjusted to control and maintain the microwave field uniformity and resonant mode, preferably the length independent mode $TM_{010}$, during the processing of the material. The applicator can thus provide microwave energy having a substantially uniform field distribution over a large area for processing materials in a non-continuous, semi-continuous or fully continuous manner.

28 Claims, 8 Drawing Sheets

FIG. 3B.
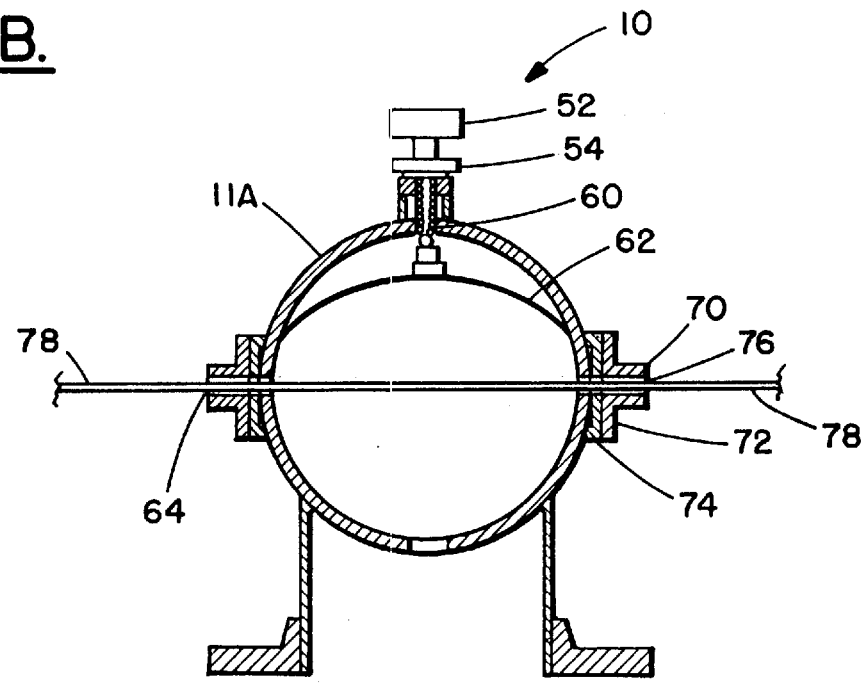
FIG. 4A.
FIG. 4B.
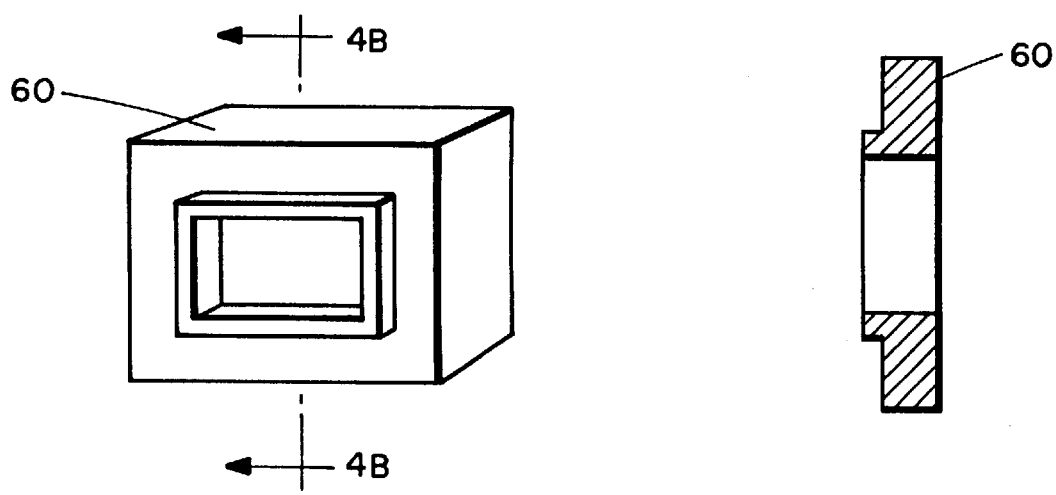

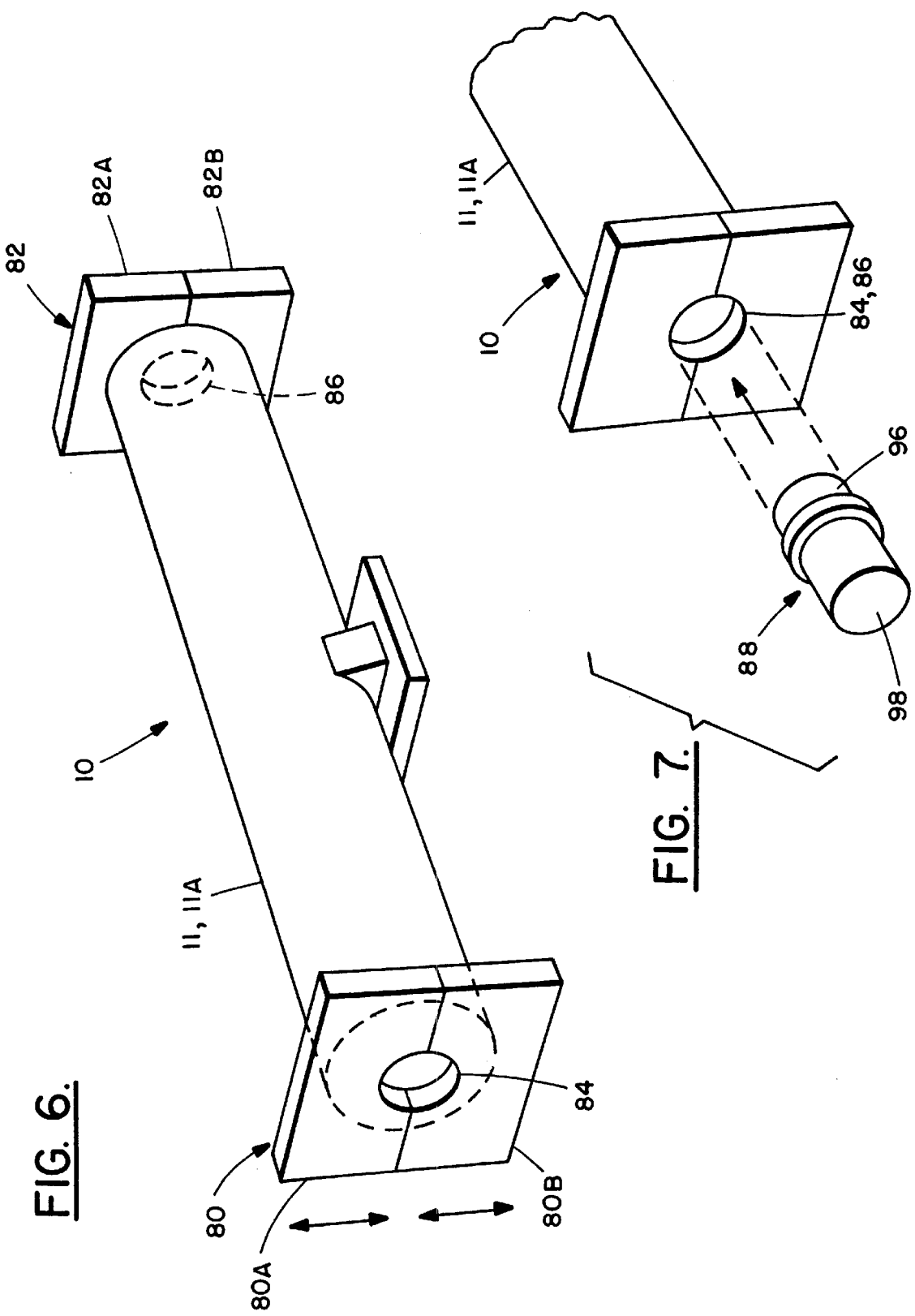

MICROWAVE APPLICATOR HAVING A MECHANICAL MEANS FOR TUNING

This application claims the priority from U.S. Provisional Application Ser. No. 60/034,718 filed Jan. 6, 1997.

FIELD OF INVENTION

The present invention is related to microwave applicators and, more particularly, to a mechanical means for tuning a microwave applicator to provide a uniform electric field.

BACKGROUND OF THE INVENTION

Microwave radiation can be applied to a material in a number of ways, using single mode, multimode applicators, traveling wave applicators, slow wave applicators, fringing field applicators and through free space. Each of the aforementioned methods of coupling microwave energy into a material has its advantages and disadvantages which usually depend on the dielectric properties, size and shape, of the materials to be processed and the type of processing (batch, continuous, . . . etc.) to be performed.

Efficient microwave energy transfer is a function of many variables as processing occurs. A number of these variables are material related, e.g., the material type and density and material temperature as well as the time history of both the material temperature and the applied electric field.

Other factors that influence coupling are related to the applicator, material geometry and size and the frequency or wavelength of the electromagnetic energy. Electromagnetic coupling depends on applicator size and geometry, material size and shape, the position of the material within the applicator, and even the relative sizes and shapes of the material and the applicator. In addition, both the applicator and material dimensions may change during heating which further complicates the efficient transfer of energy to the material.

Accordingly, a problem arises when attempting to generate a uniform microwave field across a relatively large surface for different material loads. As generally understood, if the volume of an applicator becomes too large, more than one electric field pattern can co-exist in the applicator, thereby making it multimode and introducing electric field non-uniformities. Current microwave applicators are incapable of generating a uniform microwave field across a surface that is relatively large compared to the wavelength of the radiation.

For instance, traveling wave applicators have some potential for providing uniformity. However, stray reflections, such as those that occur at the edges of a workpiece or any non-uniformity in the structure of the applicator can create standing waves leading to thermal non-uniformities. This is especially problematic in cases in which the material travels through more than one applicator and the dielectric properties of the material change depending on the processing conditions in the previous applicator.

An applicator design which shows some promise for applying uniform fields is a single mode applicator, provided that the fields can be extended over a sufficiently large region. This type of applicator can be tuned to specific electric field patterns (resonance modes) by varying the volume of the applicator.

One such approach is found in U.S. Pat. Nos. 4,507,588, 4,585,668, 4,630,566, 4,727,293, and 4,792,772 (Asmussen) all of which disclose methods and apparatuses in which a single mode resonant microwave applicator can be critically coupled by varying two separate, almost orthogonal variables, specifically the cavity length (by moving a short circuit) and the antenna position.

The Asmussen devices include a variable penetration antenna structure which acts to launch radiation into the applicator. The main advantage of the Asmussen device is that it enables complete critical coupling over a wide range of impedances (generated by the load in the applicator) and without the use of any external coupling structure. Critical coupling can thus be achieved by moving the short and the antenna appropriately.

By moving the flat part of the cavity wall (in a cylinder) in the z-direction (e.g., along the centerline of the cylinder), a wide range of electromagnetic modes can be established and maintained, even as the load varies (due to processing, e.g., temperature changing, material curing, etc.) However, one series of modes that can not be routinely excited are length independent modes, $TM_{xy0}$ and $TE_{xy0}$. The resonant frequency of these modes are only dependent on the diameter of the loaded structure. As a result, if the load changes during processing (e.g., the dielectric properties change, due to increased temperature, curing, phase change in the material and so forth), the resonant frequency in the cavity changes from an initial, fixed processing frequency, usually 2450 MHz or 915 MHz (which are the ISM bands allowed by the Federal Communication Commission (FCC)). The Asmussen devices are thus not capable of maintaining certain modes in a controlled manner, namely the length independent modes ($TM_{xy0}$ and $Te_{xy0}$) because these modes are dependent on the diameter of the applicator.

U.S. Pat. No. 5,471,037 (Goethal) discloses a single mode cylindrical applicator that operates in the $TM_{02n}$ resonant mode. The microwave applicator is designed to process monomers in order to produce prepolymers. The size of the microwave applicator is selected according to the particular monomers being processed (i.e., fixed dimension applicator). Therefore, there is no mechanism for altering the diameter of the applicator to account for substantially different loads or substantially different dielectric properties.

U.S. Pat. No. 3,461,261 (Lewis) relates to a $TM_{02n}$ applicator that processes threads and yarns with the workpieces passing along the central axis of the applicator. The dimensions of the microwave applicator are selected according to the materials being processed (i.e., fixed dimension applicator).

In general, to process wide objects in a continuous manner, such as a web or sheet like product, as found in the paper industry, lumber industry (plywood) or electronics industry (in pre-impregnated cloth for circuit board manufacture), it is desirable to be able to (i) provide a uniform electric field over the entire product for uniform heating; (ii) vary the applicator to allow for variations in the dielectric properties of a continuously moving workpiece and, thus, vary the coupling of the radiation to the product; and (iii) control the microwave power reaching the product to control the temperature-time profile of the web.

The electric field pattern sustained by the $TM_{0y0}$ series of modes, where y=1, 2 or greater, is oriented along the z-axis of the applicator and is of constant intensity along the entire length of the applicator for an empty cavity. This is an ideal mode for the processing of a web-like material. Referring to FIG. 1 (a mode chart), it can be seen that the $TM_{010}$ mode is independent of the cavity length. Therefore, a low loss, infinitely long applicator is capable of sustaining the same electric field intensity throughout the length.

There is currently no method to manipulate the dimensions of the microwave applicator, particularly the cross-sectional diameter, to maintain the resonance and achieve uniform heating of the material (load), using length independent modes. It should also be noted that all electromagnetic modes are dependent on a cross-sectional diameter of the microwave applicator (if the applicator is cylindrical or spheroid), and many have an additional dependence on the length of the applicator.

Accordingly, it is an object of the present invention to provide a microwave applicator capable of having improved energy field distribution over a wide area, as compared to the prior art.

It is also an object of the present invention to provide a microwave applicator wherein the cross-sectional area, i.e., the diameter, of the applicator can be continuously adjusted to maintain the resonance of the applicator over a wide range of dielectric loads and, thus, be able to couple microwave energy into the load.

Another object of the invention is to provide a microwave applicator capable of controlling and maintaining different resonant modes, specifically the length independent modes ($TM_{XY0}$ and $TE_{XY0}$ modes).

It is a further object of the invention to provide an elongated cylindrical microwave applicator having an adjustable cross-sectional dimension.

It is also an object of the invention to provide an elongated cylindrical microwave applicator that allows a uniform electric and magnetic field to be applied to a sheet of material being transported therethrough, in a continuous manner.

It is a further object of the invention to provide an elongated cylindrical microwave applicator that launches radiation at more than one input and provides uniform electric and magnetic fields along its length.

Another object of the invention is to provide an elongated cylindrical microwave applicator that allows a uniform electric and magnetic field to be applied to materials being transported along a longitudinal axis of the applicator.

SUMMARY OF THE INVENTION

A microwave applicator includes an elongated chamber, preferably having a cylindrical shape, for processing materials therein. A waveguide, connected to the elongated chamber, couples microwave power into the elongated chamber. The cross-sectional area of the elongated chamber can be mechanically adjusted to control and maintain the microwave field uniformity and resonant mode, preferably a length independent mode $TM_{010}$, during the processing of the material. The applicator thus provides microwave energy having a substantially uniform field distribution over a large area for processing materials in a non-continuous, semi-continuous or fully continuous manner.

It has been discovered, in the case of a cylindrical microwave applicator, that the cross-section of the applicator does not need to be perfectly circular to maintain the Transverse Magnetic (TM) or Transverse Electric (TE) resonant modes. In accordance with the discovery, the present invention provides several embodiments for adjusting the cross-sectional diameter of the applicator.

One embodiment provides an applicator that is separated into two or more parts along its length, preferably into two equal cylindrical halves. A first cylindrical half is fixed to a support structure. A second cylindrical half is mechanically adjustable towards and away from the fixed cylindrical half to increase or decrease the cross-sectional diameter of the applicator.

Another embodiment provides an applicator that has a flexible, metal foil positioned therein, between sidewalls of the applicator and along the length of the applicator such that the metal foil forms one portion of the resonant cavity. The metal foil is formed of a flexible metal whose shape can be easily altered by applying or removing pressure thereon. In this way, the cross-sectional area of the applicator can be altered by adjusting the shape of the metal foil.

BRIEF DESCRIPTION OF THE DRAWINGS

FIGS. 3A and 3B illustrate a second embodiment of a microwave applicator constructed in accordance with the present invention.

FIGS. 4A and 4B illustrates a top view and cross-sectional view of a preferred aperture.

FIG. 6 illustrates a microwave applicator of FIGS. 2, 3A and 3B for processing materials through and along a longitudinal axis of the applicator.

FIG. 7 illustrates a choke for use with the microwave applicator of FIG. 6 to prevent radiation leakage.

DETAILED DESCRIPTION OF THE INVENTION

Figure 1:
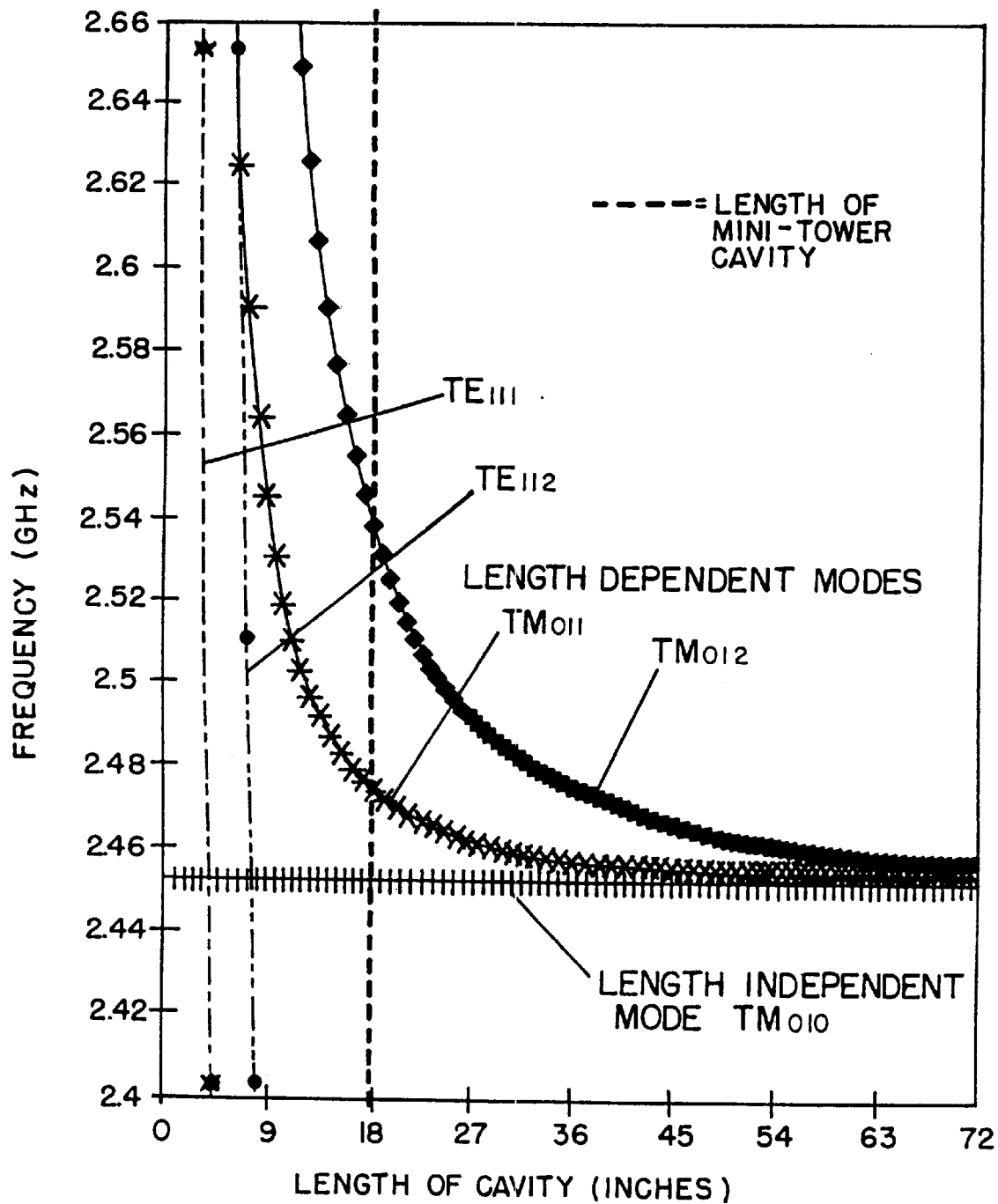
FIG. 1 illustrates a variation of resonant frequencies of different modes versus cavity length of a microwave applicator, having a cavity diameter of 3.85 inches.
Figure 2:
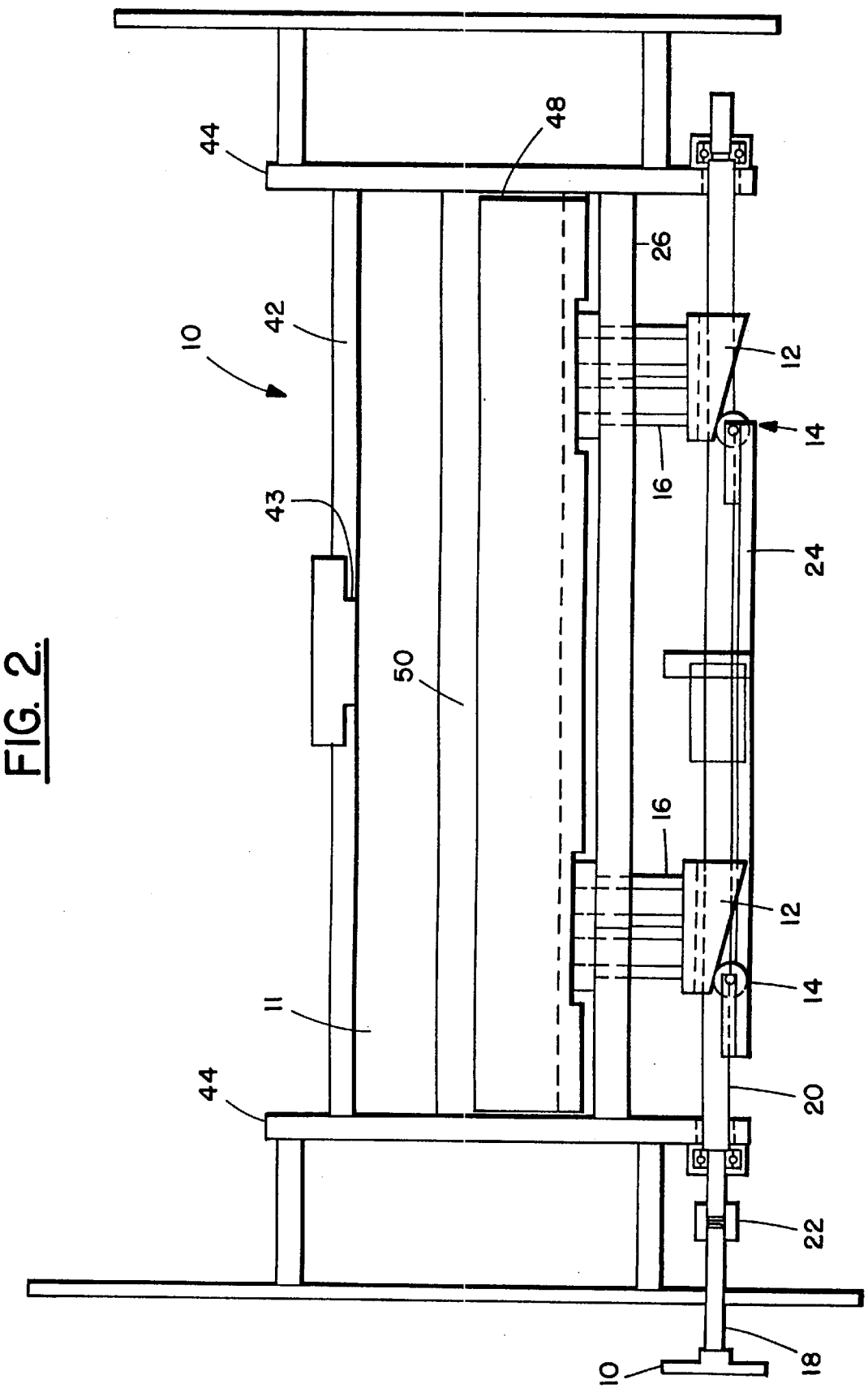
FIG. 2 illustrates a side schematic view of a first embodiment of a microwave applicator constructed in accordance with the present invention.

Referring to FIG. 2, a microwave applicator 10 in accordance with the present invention includes an elongated cylindrical chamber 11 having a resonant cavity therein. A power source is coupled to the resonant cavity preferably through a flange end waveguide extension 43. The energy is launched into cylindrical chamber 11, via waveguide extension 43. Note that, depending on the type of load or processing, the energy can be end launched from one end of the cylinder, side launched through a side wall of the cylinder or multi-launched.

It has been discovered, in the case of a cylindrical microwave applicator, that the cross-section of the cylindrical chamber does not need to be perfectly circular to maintain either a Transverse Magnetic (TM) or Transverse Electric (TE) resonant mode. This is especially the case for the $TM_{010}$ length independent mode. In other modes, such as $TE_{111}$, one mode orientation may become preferred over an infinite number of possible orientations for this mode, as the cross-section becomes grossly different from a circle (approaching an ellipse). This may be both desirable and undesirable, depending on the material to be processed.

However, if the cross-sectional deviation is too great, some modes may be suppressed or impossible to obtain, especially modes such as the $TE_{111}$ mode with strong radial fields.

Based on the above principles, it is now possible to design an elongated cylindrical applicator that can maintain the TM and TE resonant modes even though the cross-section of the applicator is not perfectly circular, e.g., an ellipse, oval, square, rectangle and so forth. The applicator can be approximately 20 percent off circular and still maintain a desired resonant mode. In light of these discoveries, the present invention provides an elongated cylindrical microwave applicator that is capable of controlling and maintaining different resonant modes, particularly the length independent modes. Various preferred forms of microwave applicator 10 will be discussed in detail below.

Referring again to FIG. 2, the first embodiment of the invention provides an applicator 10 in which the tuning capability is achieved by separating or slicing an elongated chamber 11, preferably having a cylindrical shape, into two or more parts along the length of chamber 11 (e.g., along its z-axis). These parts can be moved closer together or further apart in a continuous, uniform manner to effectively enlarge the cross-sectional area (e.g., the diameter) of the resonant cavity of the applicator. It has been discovered that the different TM and TE resonant modes can be maintained even though the cross-sectional area of chamber 11 is not perfectly circular, e.g., ellipse, oval, square, rectangle and so forth.

From an electrical perspective, it is preferable to have more than two pieces to maintain more of a circular cross-section. However, from a mechanical perspective, it is desirable to minimize the number of moving pieces. Note while the cylinder may be separated anywhere along the cylinder into two or more parts, it is preferred that elongated cylindrical chamber 11 be separated along the center-line of the cylinder to produce two approximately equal cylindrical halves 42, 48.

The mechanics involved in moving two cylindrical halves 42, 48 of chamber 11 apart in a constant manner while maintaining parallelism is non-trivial. For the pair of cylindrical halves 42, 48 preferably approximately 4 inches in diameter, a movement apart of 0.1 inches results in a change in the resonant frequency of the applicator of 60+/−3 MHz. It is thus important to be able to move the cylinders apart over the diameter range of approximately 3.6 to 4.1 inches in a uniform and controlled manner.

FIG. 2 schematically illustrates one method of moving cylindrical halves 42, 48. A first cylinder half 42 is fixed between two support structures 44; and a second cylinder half 48 floats, e.g., is allowed to slide towards and away from first cylindrical half 42. The movement of second cylinder half 48 is governed by the movement of a threaded rod 20. A knob 10 is connected to a short shaft 18 which is coupled to threaded rod 20, by a collar 22. Threaded rod 20 is also fixedly attached to a plate 24, which has preferably four roller bearings 14 attached thereto. When threaded rod 20 is turned (by rotating knob 10), the rollers travel in one direction or the other. The rollers provide a camming action on inclined planes 12, which are attached to the floating second cylinder half 48, across a spring 16. Accordingly, second cylinder half 48 can be moved towards and away from first cylindrical half 42 by rotating knob 10 in the appropriate direction. The above operation may either be performed manually or in a fully automated fashion through computer control. The second cylinder half 48 is an electrical connection with the supports 44, via flexible conductive materials.

The design of applicator 10 is useful for processing web-like materials. Such materials may be inserted into applicator 10 through a space 50 provided between first and second cylindrical halves 42, 48 (i.e., the web moves orthogonally to the plane of the drawing). As such, the range of motion of second cylindrical half 48 may be limited to provide a desired spacing between first cylindrical half 42 and second cylindrical half 48 depending on the dimensions of the materials to be processed.

However, one problem with this embodiment is that for moderately high microwave powers, there are significant electrical currents generated in the walls of the applicator, up to the skin depth of the radiation in the material, which is of the order of 2 to 5 micrometers for 2.45 GHz radiation in a metallic (e.g., brass) cylinder. If there is a break in the electrical path, there can be arcing in the applicator walls. This results in relatively a low Q factor for the applicator with lower electric field strengths and poorer performance. If the Q is too small (the tuning dip too broad), there may be sufficient overlap between modes that spurious (undesirable) modes will be supported simultaneously, resulting in a multimode applicator with poor uniformity control or by not being able to support the desired mode.

Figure 3A:
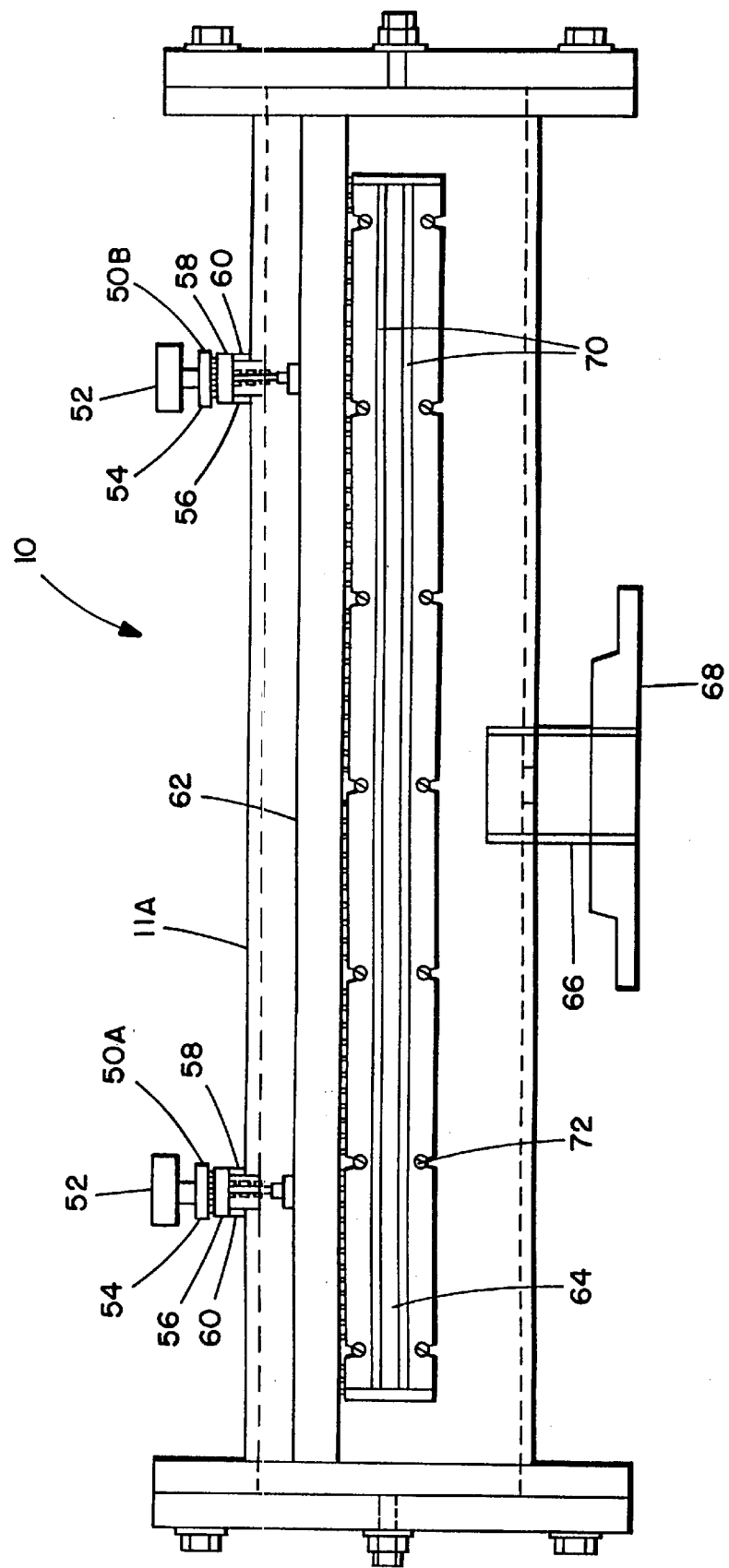

Referring to FIGS. 3A and 3B, a second embodiment of the invention provides an alternative approach for adjusting the cross-sectional area of an elongated chamber 11A, preferably having a cylindrical shape. Instead of separating the cylindrical chamber into two or more movable parts, the second embodiment includes a flexible metal foil 62 positioned inside the resonant cavity of cylindrical chamber 11A. Metal foil 62 is secured between the side walls of the resonant cavity and runs along the length of the cylinder such that it forms one portion or wall of the resonant cavity. As metal foil 62 is made of a flexible, conductive material (e.g., a beryllium/copper alloy or plated spring steel), the cross-sectional dimensions of the resonant cavity can be varied by simply applying an appropriate amount of pressure to metal foil 62, as shown in FIG. 3B. The greater the pressure, the more metal foil 62 reduces the cross-sectional diameter of the cavity of cylindrical chamber 11A. Conversely, the less the pressure, the greater the curvature of metal foil 62 and the larger the cross-sectional diameter of the cavity of cylindrical chamber 11A. As such, the cross-sectional shape of metal foil 62 can be adjusted to obtain a desired cavity diameter.

Referring to FIG. 3A, one mechanical method of applying pressure to metal foil 62 is shown. In particular, two adjustment mechanisms 50A, 50B enable a changing of the curvature of metal foil 62 and, thus, the cross-sectional diameter of the resonant cavity. Each adjustment mechanism 50A, 50B includes a head screw 52 having a threaded rod 60 coupled to metal foil 62, via tubular opening 56. The top planar surface of each tubular opening 56 has a cap 58 thereon with a threaded opening and a knurled check nut 58 for receiving threaded rod 60 therethrough. Knurled check nut 58 is positioned on the top of cap 58 to limit the range of motion of threaded rod 60. Accordingly, the diameter of the resonant cavity can be varied by rotating the head screws 52 in the appropriate direction and, thus, changing the cross-sectional shape of metal foil 62 to a desired curvature. The above operation may either be performed manually or in a fully automated fashion through computer control.

Note that while only two adjustment mechanisms 50A, 50B are illustrated in FIG. 3, applicator 10 may include any number of such adjustment devices. It is preferred that the adjustment mechanisms are evenly positioned along the length of the cylindrical applicator such that pressure can be applied uniformly across the flexible metal foil. The main reason is to ensure that the flexible metal foil maintains a uniform cross-sectional arcuate shape, e.g., curvature, along the length of the cylindrical applicator.

In order to process sheet-like material, cylindrical chamber 11A preferably includes two product openings 64 extending across the length of the cylinder and positioned on opposing sides of chamber 11A. The material to be processed is inserted through one opening and exits through the other opening. Each opening 64 is defined by a slot 76, an angle platform 74 and two L-shaped ridges 70 diametrically positioned above and below slot 76 of cylindrical chamber 11A. Angle platform 74 and L-shaped ridges extend along the length of opening 64 and are connected to cylindrical chamber 11A by screws 72. When connected, the above components form an upper and lower ridge having a space therebetween. The material to be processed can be inserted into and out of the cavity of cylindrical chamber 11A, via openings 64. It is important to understand that the extending ridges support the material as it is being processed and ensure that the material is fed into applicator 10 along a central horizontal axis.

The cylindrical chamber 11A may be an aluminum tube having a thickness of approximately 0.250 inches and a length of approximately 19.750 inches. Flexible metal foil 62 is metal plate preferably made of a beryllium/copper alloy and having a thickness of approximately 0.003 inches, a length of approximately 17.250 inches and a width of approximately 3.850 inches.

Applicator 10, as described above in the first and second embodiments, may be employed in various applications for continuous or semi-continuous processing of web or sheet-like materials through a center-feed of elongated chamber 11, 11A (FIGS. 2 and 3). Examples of such applications include drying paper and textile products (woven and non-woven), curing of coatings, processing of carpet backing and drying and fixing of inks (one color or multi-color). When drying and fixing inks, applicator 10 can be used to process all colors simultaneously or each color individually before a next color is applied. Applicator 10 may also be employed in an application involving both curing and drying, such as the formation of prepreg.

In the above-noted applications, a uniform field over the full width of the web is important and critical. As the weight of the web (fiber density, etc.), the moisture content (entering or exiting) or the thickness of the coating is varied, the cross-sectional area, particularly the diameter, of the applicator can be varied to control uniformity and mode of microwave energy therein during processing of the material.

Applicator 10 is particularly useful over conventional methods for heating of paper-type products, e.g., to dry toner or ink on paper (printed publications) or to remove water from the paper. Conventional heating methods involve the direct application of heat at high temperatures onto the paper, resulting in the thermal degradation of the cellulose of the heated paper. In other words, direct heating of the paper burns and damages the cellulose of the paper. Unlike conventional methods, the present invention couples uniform microwave energy directly to the water, toner or ink (e.g., liquid) on or in the paper and, thus, heats the liquid and not the paper. As a result, there is substantially less degradation of the cellulose in the paper.

Applicator 10 may also be utilized in the formation of a continuous film. Conventionally, the film material is dissolved in a solvent or is carried as a water-based emulsion. The liquid is extruded from a wide opening onto a heated drum where most of the solvent is removed from a very weak but continuous film. Thereafter, the now continuous film is heated to remove the remaining solvent to generate the final properties of the film. However, by utilizing, applicator 10 preferably in the $TM_{010}$ mode, it is possible to use microwave energy to remove the solvent with a shorter process length than is possible conventionally. Since the "green strength" of an incompletely processed film is generally extremely poor, such an approach causes less damage and yield loss than if the film passes over an excessive number of rollers to support the longer process length.

Figure 8A:
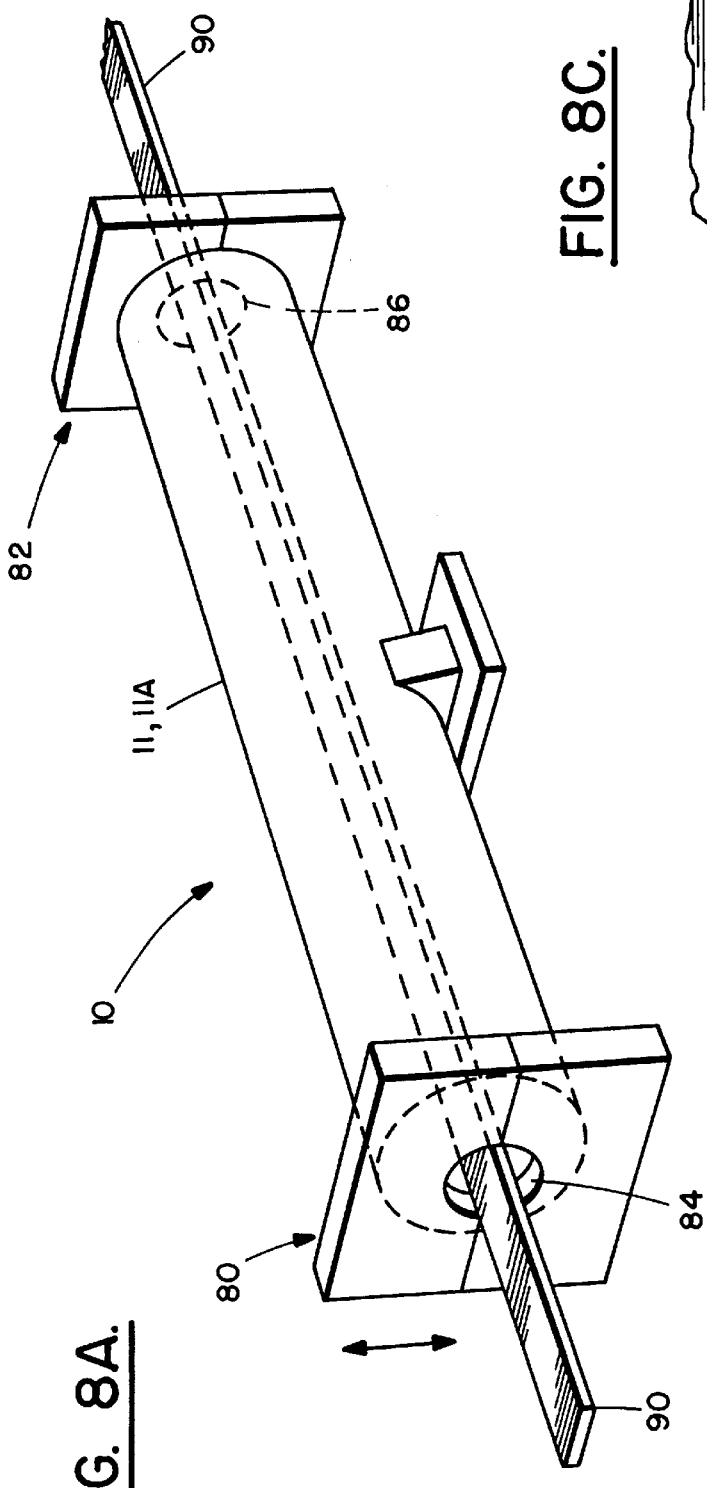
FIG. 8A illustrates a conveyor belt in the microwave applicator of FIG. 6 to provide for continuous processing of materials.
Figure 8C:
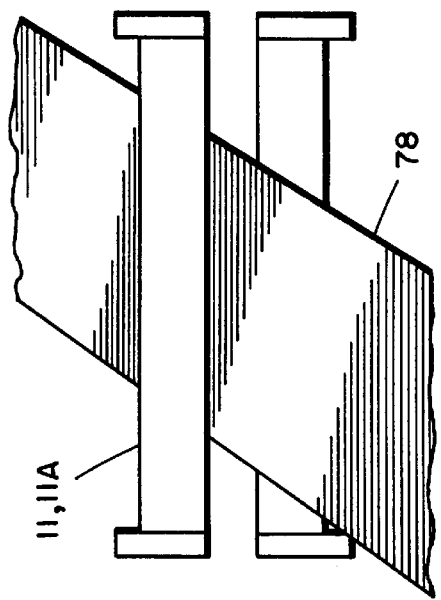
FIG. 8C illustrates a conveyor belt running through a central opening of the microwave applicator of the first and second embodiments in FIGS. 2, 3A and 3B.

Applicator 10 may also include a conveyor belt 78 passing through the center openings along the length of elongated chamber 11, 11A, as shown in FIGS. 3B and 8C. A semi-continuous or fully continuous feed of materials can be carried by conveyor belt 78 through the internal cavity of elongated chamber 11, 11A. Such a system may be utilized for printed circuit boards in order to cure or dry coat solder masks, to die attach adhesives or to underfill (resin applied below a chip to encapsulate the electrical connection), to glob top resins and so forth. Similarly, applicator 10 may be employed in the manufacture of a tape product with a periodic pattern such as TAB (tape automated bonding) tape, which is typically copper patterned structures on a Kapton polymide (manufactured by DuPont™) and optionally with electronic devices or structures attached.

While both the applicators of the first and second embodiments have been described above for continuous processing of web or sheet-like materials along a center-feed as shown in FIGS. 2 and 3, such applicators may also be configured to process materials such as annular fiber bundles or extrudates along longitudinal axis of the elongated chamber in a continuous manner. This is accomplished by providing an entry opening in one end support structure of the applicator to allow the materials to be end-fed into the applicator and an exit opening positioned on the other end support structure to allow the processed materials to pass through the applicator. It has been discovered that the cross-sectional diameter of the entry and exit openings can be up to one-half the cross-sectional diameter of the applicator without affecting the performance of the applicator. A more detailed explanation of such end-fed applicator is provided below.

Referring to FIG. 6, an applicator 10 includes an elongated chamber 11, 11A having the cross-sectional area adjusting means of the above first or second embodiments shown in FIGS. 2 and 3. Applicator 10 further includes support structures 80, 82 (e.g., endplates) positioned at either ends of elongated chamber 11, 11A. Support structure 80 includes an entry opening 84, preferably centrally positioned thereon, for receiving material to be processed. Support structure 82 also includes an opening 86 (hereinafter exit opening), preferably centrally positioned thereon, for allowing materials processed in elongated chamber 11, 11A to exit therethrough. It is preferred that exit opening 86 be aligned with entry opening 84 so that materials to be processed can be continuously fed into and out of elongated chamber 11, 11A along a longitudinal axis of elongated chamber 11, 11A.

In order to accommodate the reception of materials of various sizes and shapes into elongated chamber 11, 11A, support structures 80, 82 thereon can be split into two or more movable pieces to enlarge or contract the cross-sectional area of openings 84, 86 respectively. As previously discussed, the cross-sectional diameter of openings 84, 86 can be varied up to approximately one-half the cross-sectional diameter of elongated chamber 11, 11A without affecting the performance of applicator 10. By combining the cross-sectional area adjusting means of the first or second embodiments with the variable end-feed mechanism as described above, various types of materials (having different sizes, shapes and properties) can be fed into elongated chamber 11, 11A by varying the cross-sectional area of entry opening 84 to allow the material to pass therethrough, processed in a uniform manner in elongated chamber 11, 11A by adjusting the cross-sectional area of elongated chamber 11, 11A (as described above in the first and second embodiments), and fed out of elongated chamber 11, 11A by varying the cross-sectional area of exit opening 86 to allow the processed material to exit therethrough. The cross-sectional area of openings 84, 86 can either be adjusted before or during processing in accordance with the size and shape of the material to be processed.

It is preferred that support structure 80 is split into two halves 80A, 80B which can be moved towards and away from each other to decrease or increase respectively the cross-sectional area of entry opening 84. As with support structure 80, support structure 82 is preferably split into two halves 82A, 82B and can be moved towards and away from each other to decrease or increase respectively the cross-sectional area of opening 86. It should be noted that good electrical contact can be maintained between elongated chamber 12 and support structures 80, 82 through the use of metal frequencies, metal bands or the like.

Halves 80A, 80B of support structure 80 and halves 82A, 82B of support structure 82 can either be manually adjusted by an operator or automatically adjusted by a computer controlled unit according to the materials being processed. In this way, applicator 10 may be utilized to process materials having various sizes and shapes in a continuous or semi-continuous manner.

However, as the size of openings 84, 86 increases, the amount of radiation leakage from the openings increases. To remedy this problem, applicator 10 may include a choke 88, as shown in FIG. 7, to prevent radiation leakage from entry opening 84. Choke 88 includes an open-ended cavity 98 to allow materials to pass therethrough and an end portion 96 with an exterior mating surface configured to mate with entry opening 84. When end portion 96 of choke 88 is positioned into entry opening 84, the exterior mating surface of choke 88 forms a seal with the interior surface of opening 84 and, thus, prevents leakage of radiation from elongated chamber 11, 11A during processing of the material.

While one choke 88 is shown in FIG. 7 to mate with entry opening 84, there may also be included an additional choke 88 to prevent radiation leakage from exit opening 86. As with entry opening 84, choke 88 can be positioned in exit opening 86 to form a seal therebetween to prevent leakage of radiation, and the materials processed in elongated chamber 11, 11A can exit elongated chamber 11, 11A through the open-ended cavity of choke 88. The length of choke 88 should be a multiple of one-fourth (¼) of the wavelength of the radiation length used to process the material.

Figure 8B:
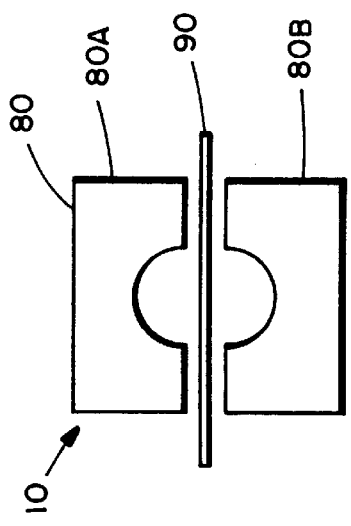
FIG. 8B illustrates a conveyor belt having a cross-sectional width greater than the cross-sectional width of the elongated chamber in the microwave applicator of FIG. 8A.

Referring to FIGS. 8A and 8B, applicator 10 may further include a conveyor belt 90 having a portion running between openings 84, 86 along a longitudinal axis of the chamber. Conveyor belt 90 can feed materials through elongated chamber 11, 11A at various processing speeds, in a continuous or semi-continuos manner, depending on the material's properties such as the size, shape, dielectric constant and desired heating period. Conveyor belt 90 provides an easy method for continuously or semi-continuously feeding materials through elongated chamber 11, 11A.

Conveyor belt 90 preferably comprises a substantially non-microwave absorbing material (or minimally microwave absorbing material) such as Teflon coated glass fiber or uncoated woven glass fiber; non-woven, non-reinforced Teflon; or polypropylene. Non-reinforced systems may be utilized even though they will not maintain dimensional tolerances. It is also preferred that conveyor belt 90 runs along a substantially central longitudinal axis of chamber 11, 11A.

Figure 9:
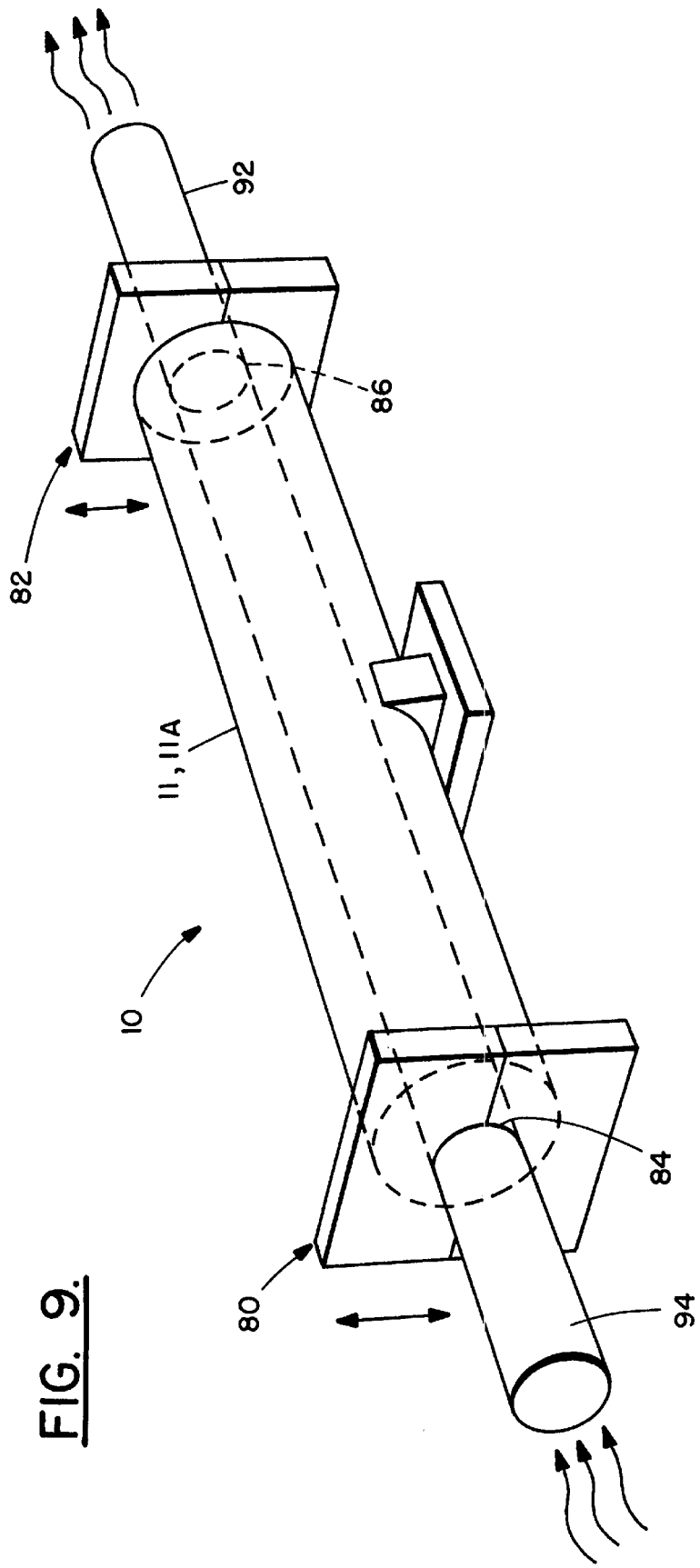
FIG. 9 illustrates a tube in the microwave applicator of FIG. 6 to provide for continuous processing of liquid-based materials.

Applicator 10 may also be employed to process liquid-based materials or fluids. As shown in FIG. 9, applicator 10 may include a non-metallic tubular or concentric structure 94 running along longitudinal axis of elongated chamber 11, 11A (e.g., along the length of elongated chamber 11, 11A). It is preferred that tubular structure 94 runs along a substantially center longitudinal axis of elongated chamber 11, 11A. A reactant stream of the liquid (to be processed) flows through tubular structure 94 and is processed accordingly. Applicator 10 can thus be employed to heat any material in liquid form, such as organic reactants, to increase or decrease the speed of a chemical reaction. Elongated chamber 11, 11A can be oriented in a vertical or horizontal direction and the reactant flow can also be in any direction.

As can be appreciated by those skilled in the art, such an arrangement provides a cold wall reactor with a heating zone typically in a portion of tubular structure 94 that is central of elongated chamber 11, 11A, e.g., where the microwave energy is propagated into elongated chamber 11, 11A. Therefore, microwave energy is directly coupled to the reactant stream, while the tubular structure 94 remains unaffected and cool (except possibly for heat conduction by the heated liquid). It is important to understand that a cool wall reactor (e.g., tubular structure 94), as disclosed in the present invention, avoids the heating non-uniformities caused by hot wall reactors such as those found in conventional heating systems. As commonly understood by those skilled in the art, materials processed in contact or proximity with hot walls are subjected to additional heating, thereby resulting in non-uniform heating of the material.

The incorporation of tubular structure 94 also enables corrosive liquids such as acids to be processed so as not to damage or corrode the metallic surface of elongated chamber 11, 11A. For instance, hydrofluoric acid may be injected into tubular structure 94 and heated to a desired temperature in applicator 10, without damaging the surface of elongated chamber 11, 11A.

Although only one applicator 10 has been described above for use in the continuous processing (end-feed or center-feed) of various types of materials, a multiple zone arrangement to control the heating rate and thermal ramp can also be utilized in the processing of thin sheet polymeric or composite materials. For example, in the processing of prepreg, the initial stage involves the removal of solvent (e.g., drying). Subsequently, the resin is advanced to a partial state of cure. In conventional processing, this is accomplished by fixing the temperature of different zones to achieve a particular thermal profile.

In the present invention, a similar thermal profile can be achieved by passing the material being processed through multiple microwave applicators 10 positioned in series, where the material is fed from one microwave applicator to the next. If the dielectric properties of the material load continually change during processing, the resonant frequency of each microwave applicator must be varied to accommodate the property change. This can be accomplished through the cross-sectional area adjusting means described. In the case where the material load goes through significant changes, the structural dimensions of each individual microwave applicator 10 is configured to account for the different property changes. The benefits of such a multi-zone or multi-pass microwave applicator arrangement is that increased process control is attained.

In addition to the continuous processing methods as described above, elongated chamber 11, 11A of the first and second embodiment (FIGS. 2 and 3) may also be employed to batch process materials. Either of the two support plates 44 (endplates) of applicator 10 may be configured to be movable to an open and closed position (e.g., hinge coupled) or removable. During the operation of the invention, support structure 44 is moved to an open position or removed to allow loading of elongated chamber 11, 11A. After processing, support structure 44 is moved to an open position or removed and the processed material is removed. Note that support structure 44 can be driven by a piston to automate the processing and withdrawn on the same axis as the applicator or can be pivoted around one point, depending on the type of material to be loaded and the type of electrical contact between elongated chamber 12 and support structure 44. The end-plates can also be moved a short distance along the axis of applicator 10 and then rotated. Such an applicator system can be used to heat semiconductor wafers or to cure or anneal coatings of layers.

For both the first and second embodiments, microwave radiation can be coupled into applicator 10 using an iris, loop or antenna placed on the outer surface of the applicator or from the end of the applicator (e.g., end launch). The choice between the aforementioned devices depends on the material to be processed, the manner in which the dielectric properties change during processing and the resonant mode being utilized. Multiple launchers can also be used to improve uniformity and to generate higher power levels in the cavity.

Figure 5:
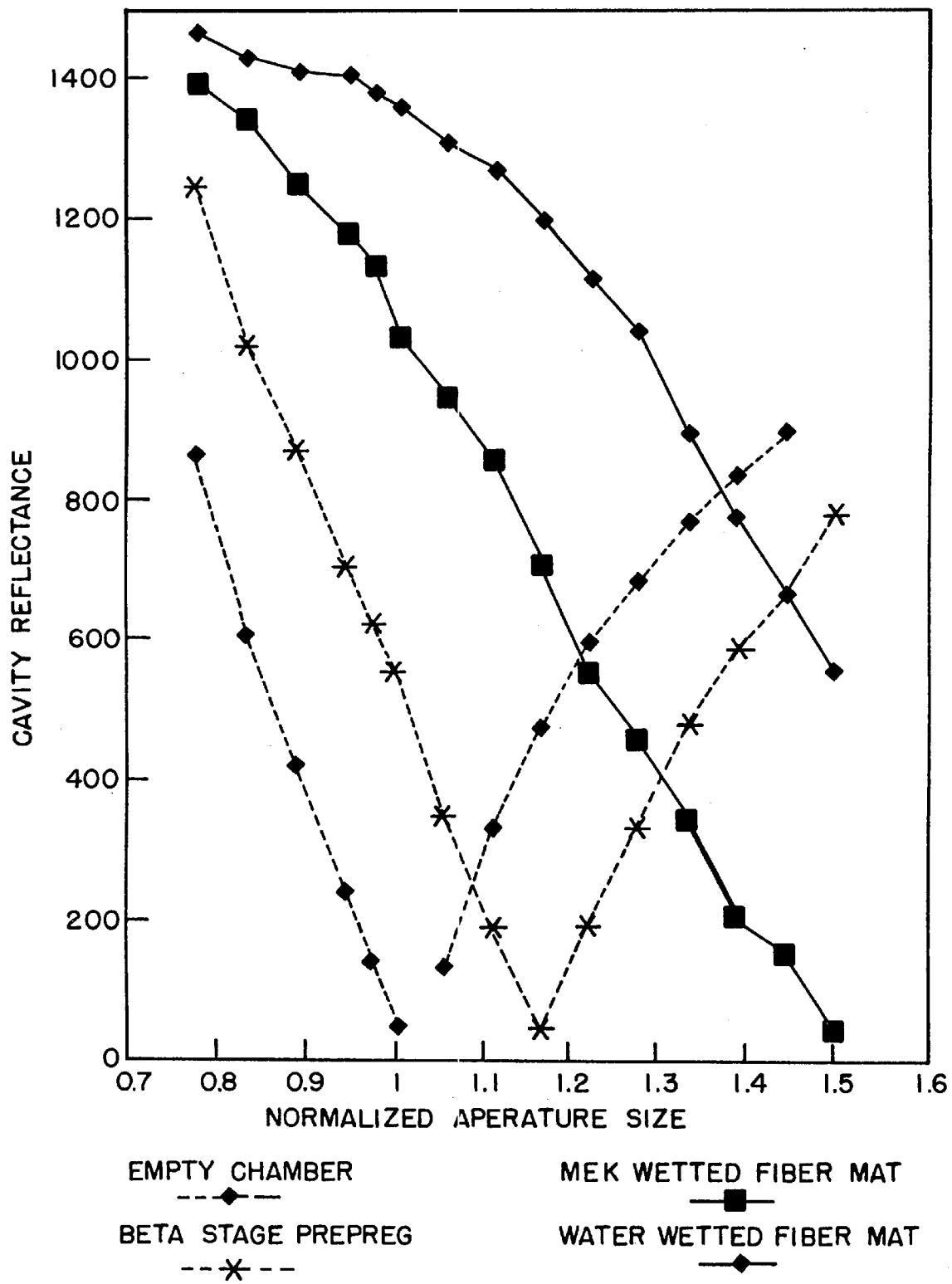
FIG. 5 illustrates a graph explaining the different loads affect on the optimum aperture size.

For cases in which a continuously moving web passes through applicator 10, the dielectric properties of the web reach a steady state after an initial period and change only minimally thereafter. In this case, provided that sufficient microwave energy can be coupled into microwave applicator 10 in the initial period to heat and process the web, only minimal variation in the coupling method is required to effectively match the impedance of applicator 10 and obtain substantially complete coupling of the microwave energy into the applicator. An iris or an aperture can be used such, as shown in FIGS. 4A and 4B. The size of the opening is selected before processing to account for a particular load and, thus, can not be varied during processing. The effect of different loads on the coupling efficiency and aperture size is shown in FIG. 5. A movable iris would also be used.

When the iris is placed on the outer wall of the applicator 10 and the fundamental mode of the launch waveguide is utilized, the length independent $TM_{0n0}$ modes are preferably selected. However, whenever there is a load in applicator 10 this provides a means for mode switching to other modes if the resonant frequency for that mode matches the microwave frequency. This problem is exacerbated as the length of the applicator is increased substantially since the normally length dependent modes can now be selected or sustained.

A continuously variable antenna can be used to couple microwave energy into the applicator in two modes, e.g., either through a sidewall launch if the TE modes are desired or through an end launch if the TM modes are desired to be excited. Such a device can be constructed in a similar manner to that of U.S. Pat. Nos. 4,507,588, 4,585,668, 4,630,566, 4,727,293, and 4,792,772 (Asmussen). Similarly, a coupling loop (e.g., a magnetic loop) can be utilized in either an end-launch configuration if the TE modes are desired or a side launch configuration if the TM modes are desired.

In the operation of the invention, when a material load is placed in the empty resonant cavity of the applicator 10, each electromagnetic resonance is shifted down in frequency and Q is lowered. The presence of the material load adds an additional material conductance and susceptance to the circuit. These additional circuit elements are functions of the material load placement, volume, shape and material properties.

The material load is irradiated with microwave energy by first adjusting the cross-sectional diameter of the cavity of applicator 10, as described above for the first and second embodiments. The specific resonant mode chosen depends on the shape and location of the material load. Once adjusted for a match in a pre-specified mode, preferably the length independent mode $TM_{010}$, microwave power is then applied and absorbed into the resonant cavity without reflection; and heating of the material then begins. As the material is heated, the material properties are altered, thereby resulting in a shift in the cavity resonance and a change in the input impedance of the applicator. In order to compensate for the changing material properties (e.g., the dielectric constant) during processing, the cross-sectional diameter of the applicator is varied iteratively until reflected power is reduced to zero, e.g., the applicator is matched as the material properties change. The tuning process can be quickly performed either manually or automatically by computer control as described above.

In addition to resonant mode selection and matching, the mechanical tuning feature of the present invention serves other practical functions as described below. For instance, it allows different material loads to be matched to a given constant frequency power source. Variations in the cavity resonant frequency caused by (1) the cavity expansion or contraction due to ambient temperature changes and (2) relative humidity changes in the air inside the resonant cavity can also be cancelled. Frequency drifts caused by variations in output power and heating of a power oscillator can be compensated for by mechanical tuning. Finally, it allows the applicator to be used with power oscillators which oscillate at different frequencies.

In summary, the applicator of the present invention can be utilized for a large range of materials processing applications, including solid materials processing and plasma processing in addition to the continuous processing of sheet. As described above, a complete series of modes can be achieved by varying the diameter of the applicator, and some may be more advantageous for a particular process. For example, the processing of silicon wafers using microwave energy has been found to be most effective utilizing the $TE_{111}$, $TM_{011}$ and has been theorized for the $TM_{010}$ modes to provide maximum uniformity over the workpiece. The latter cannot normally be selected since the dielectric properties change substantially during heating and processing, and hence a variable diameter applicator is the only method by which it can be selected and maintained during processing.

The invention having thus been described with particular reference to the preferred forms thereof, it will be obvious that various changes and modifications may be made therein without departing from the spirit and scope of the invention as defined in the appended claims.

We claim:

1. An apparatus for applying microwave energy having a substantially uniform field distribution over a large area for processing a material, said apparatus comprising:

an elongated chamber having means for receiving said material at one end of a longitudinal axis of said elongated chamber;

adjustment means associated with said elongated chamber for adjusting a cross-sectional area of said elongated chamber to control uniformity and mode of microwave energy in said elongated chamber during processing of said material;

means for coupling microwave power into said elongated chamber; and wherein said means for receiving includes a first endplate and a second end plate respectively positioned at opposite ends of said elongated chamber, said first endplate including a first opening and said second endplate including a second opening, wherein said material enters said elongated chamber through one of said first opening and said second opening and exits said elongated chamber through the other of said first opening and said second opening.

2. An apparatus as recited in claim 1, wherein said first endplate is movably connected to said one end of said elongated chamber.

3. An apparatus as recited in claim 1, wherein said first endplate is detachably connected to said one end of said elongated chamber.

4. An apparatus as recited in claim 1, wherein said first endplate includes means for adjusting a cross-sectional area of said first opening.

5. An apparatus as recited in claim 1, wherein said first opening has a cross-sectional diameter up to approximately one-half of a cross-sectional diameter of said elongated chamber.

6. An apparatus as recited in claim 1, further comprising a first choke, associated with said first opening, for preventing radiation leakage from said first opening.

7. An apparatus as recited in claim 1, wherein said second endplate further comprises means for adjusting a cross-sectional diameter of said second opening.

8. An apparatus as recited in claim 1, wherein said second opening has a cross-sectional diameter up to approximately one-half of a cross-sectional diameter of said elongated chamber.

9. An apparatus as recited in claim 1, further comprising a second choke, associated with said second opening, for preventing radiation leakage from said second opening.

10. An apparatus as recited in claim 1, further comprising means for holding said material having a liquid form, wherein said means for holding includes a portion running between said first and second openings.

11. An apparatus as recited in claim 10, wherein said means for holding comprises a tubular structure.

12. An apparatus as recited in claim 11, wherein said tubular structure runs along a substantially central longitudinal axis of said elongated chamber.

13. An apparatus as recited in claim 11, wherein said tubular structure comprises a substantially non-microwave absorbing material.

14. An apparatus as recited in claim 13, wherein said conveyor belt comprises a perfluorinated hydrocarbon.

15. An apparatus as recited in claim 13, wherein said tubular structure comprises quartz.

16. An apparatus as recited in claim 1, further comprising means for feeding said material through said longitudinal axis of said elongated chamber, said means for feeding having a portion running between said first opening and said second opening.

17. An apparatus as recited in claim 16, wherein said means for feeding comprises a conveyor belt.

18. An apparatus as recited in claim 17, wherein said conveyor belt comprises a substantially non-microwave absorbing material.

19. An apparatus as recited in claim 18, wherein said conveyor belt comprises a perfluorinated hydrocarbon.

20. An apparatus as recited in claim 16, wherein said means for feeding feeds said material continuously through said longitudinal axis of said elongated chamber.

21. An apparatus as recited in claim 16, wherein said means for feeding feeds said material semi-continuously through said longitudinal axis of said elongated chamber.

22. A system for processing materials comprising at least two apparatuses of claim 1 positioned in series to one another, wherein said material processed in one of said two apparatuses is fed into the other of said two apparatuses.

23. A method for processing a material in a microwave applicator comprising an elongated chamber having a first end and a second end opposite said first end, said method comprising the steps of:

(a) feeding said material into said elongated chamber through one of said first end and said second end;

(b) coupling microwave energy to said material in said elongated chamber; and (c) adjusting a cross-sectional area of said elongated chamber to control uniformity and mode of microwave energy, during processing of said material.

24. The method as recited in claim 23, further comprising the step (d) of removing said material from said one of said first end and said second end, after processing of said material.

25. The method as recited in claim 23, further comprising the step (e) of feeding said material out of said elongated chamber through the other of said first end and said second end.

26. The method as recited in claim 25, wherein said material is fed continuously through said elongated chamber.

27. The method as recited in claim 25, wherein said material is fed semi-continuously through said elongated chamber.

28. The method as recited in claim 25, wherein said material is fed through said elongated chamber along a substantially central longitudinal axis of said elongated chamber.

* * * * *